United States Patent
Grandbois et al.

(10) Patent No.: US 10,788,751 B2
(45) Date of Patent: Sep. 29, 2020

(54) COATING COMPOSITION FOR USE WITH AN OVERCOATED PHOTORESIST

(71) Applicants: Rohm and Haas Electronic Materials LLC, Marlborough, MA (US); Rohm and Haas Electronic Materials Korea Ltd., Cheonan, Chungcheongnam-Do (KR)

(72) Inventors: Matthew Grandbois, Marlborough, MA (US); Myung Yeol Kim, Chungcheongnam-Do (KR); Eui Hyun Ryu, Chungcheongnam-Do (KR); Jae Hwan Sim, Chungcheongnam-Do (KR); Min Kyung Jang, Chungcheongnam-Do (KR); Jung-June Lee, Chungcheongnam-Do (KR)

(73) Assignees: Rohm and Haas Electronic Materials LLC, Marlborough, MA (US); Rohm and Haas Electronic Materials Korea Ltd., Cheonan, Chungcheongnam-do (KR)

( * ) Notice: Subject to any disclaimer, the term of this patent is extended or adjusted under 35 U.S.C. 154(b) by 0 days.

(21) Appl. No.: 15/253,005

(22) Filed: Aug. 31, 2016

(65) Prior Publication Data
US 2017/0059991 A1 Mar. 2, 2017

Related U.S. Application Data

(60) Provisional application No. 62/212,095, filed on Aug. 31, 2015.

(51) Int. Cl.
| | |
|---|---|
| *G03F 7/11* | (2006.01) |
| *G03F 7/09* | (2006.01) |
| *C09D 167/00* | (2006.01) |
| *C09D 5/00* | (2006.01) |
| *C07D 487/04* | (2006.01) |
| *H01L 21/02* | (2006.01) |
| *H01L 21/027* | (2006.01) |
| *H01L 21/308* | (2006.01) |
| *C08L 61/06* | (2006.01) |
| *C08G 8/04* | (2006.01) |
| *C08K 5/3445* | (2006.01) |

(52) U.S. Cl.
CPC .......... *G03F 7/091* (2013.01); *C07D 487/04* (2013.01); *C08G 8/04* (2013.01); *C08L 61/06* (2013.01); *C09D 5/006* (2013.01); *C09D 167/00* (2013.01); *G03F 7/11* (2013.01); *H01L 21/0274* (2013.01); *H01L 21/0276* (2013.01); *H01L 21/02112* (2013.01); *H01L 21/02282* (2013.01); *H01L 21/3081* (2013.01); *C08K 5/3445* (2013.01)

(58) Field of Classification Search
CPC . G03F 7/11; G03F 7/091; G03F 7/094; G03F 7/0045; G03F 7/40; G03F 7/16; G03F 7/168; H01L 21/0274; H01L 21/0276; H01L 21/3081; H01L 21/02112; H01L 21/02282; C08G 8/04; C09D 5/006; C08L 61/06
USPC ............ 430/270.1, 322, 325, 329, 330, 331; 438/703, 781; 528/153
See application file for complete search history.

(56) References Cited

U.S. PATENT DOCUMENTS

| | | | |
|---|---|---|---|
| 7,416,821 B2 | 8/2008 | De et al. | |
| 7,638,262 B2 | 12/2009 | Wu et al. | |
| 7,691,556 B2 | 4/2010 | Wu et al. | |
| 7,727,705 B2 * | 6/2010 | De ........................... | G03F 7/11 |
| | | | 430/270.1 |
| 8,142,988 B2 | 3/2012 | Zampini et al. | |
| 8,334,338 B2 | 12/2012 | Yoshimura et al. | |
| 8,465,902 B2 | 6/2013 | Yao et al. | |
| 8,986,918 B2 * | 3/2015 | Breyta .................. | G03F 7/0045 |
| | | | 430/270.1 |
| 2007/0026458 A1 | 2/2007 | Polidori et al. | |
| 2008/0176165 A1 | 7/2008 | Xiang et al. | |
| 2010/0009289 A1 | 1/2010 | Fedynyshyn | |

(Continued)

FOREIGN PATENT DOCUMENTS

| | | |
|---|---|---|
| CN | 103370653 A | 10/2013 |
| JP | 2006215180 A | 8/2006 |

(Continued)

OTHER PUBLICATIONS

Machine translation of JP 2012-133289 (no date).*

(Continued)

*Primary Examiner* — Amanda C. Walke
(74) *Attorney, Agent, or Firm* — Mintz Levin Cohn Ferris Glovsky and Popeo, P.C.; Peter F. Corless

(57) ABSTRACT

Organic coating compositions, particularly antireflective coating compositions for use with an overcoated photoresist, are provided that comprise that comprise a crosslinker component that comprises a structure of the following Formula (I):

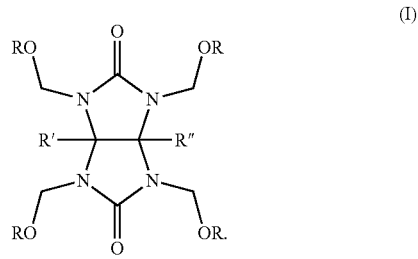

13 Claims, No Drawings

(56) References Cited

U.S. PATENT DOCUMENTS

| | | | |
|---|---|---|---|
| 2010/0021830 A1* | 1/2010 | Kim | G03F 7/091 430/5 |
| 2010/0029556 A1 | 2/2010 | Dey et al. | |
| 2010/0092894 A1 | 4/2010 | Liu et al. | |
| 2010/0109980 A1* | 5/2010 | Tohara | G02B 27/0172 345/32 |
| 2010/0151381 A1* | 6/2010 | Tachibana | C09D 133/16 430/270.1 |
| 2010/0207276 A1* | 8/2010 | Allen | H01L 21/02137 257/773 |
| 2010/0221657 A1* | 9/2010 | Sakamoto | C08G 59/1438 430/270.1 |
| 2011/0155944 A1* | 6/2011 | Cho | C07C 33/26 252/62.51 R |
| 2012/0202155 A1* | 8/2012 | Yao | C09D 161/24 430/311 |
| 2012/0270994 A1* | 10/2012 | Kim | G03F 7/091 524/553 |
| 2013/0313643 A1 | 11/2013 | Doris et al. | |

FOREIGN PATENT DOCUMENTS

| | | |
|---|---|---|
| JP | 2007090861 A | 4/2007 |
| JP | 2012133289 A * | 7/2012 |
| WO | 2007112934 A1 | 10/2007 |
| WO | 2012107823 A1 | 8/2012 |
| WO | 2014185335 A1 | 11/2014 |

OTHER PUBLICATIONS

English language summary of Office Action dated May 12, 2017 issued in counterpart Taiwan Application 106-2(6) 01195-10620513800, 4 pages.

English language summary of Office Action issued in counterpart Korean Application 10-2016-0109283, 3 pages.

English language summary of Office Action of counter Japanese application 2016?166180.

English language summary of Office Action of counterpart Chinese application: 201610742216.4.

* cited by examiner

COATING COMPOSITION FOR USE WITH AN OVERCOATED PHOTORESIST

CROSS-REFERENCE TO RELATED APPLICATION

This application claims priority to U.S. Provisional Application No. 62/212,095, filed Aug. 31, 2015. The contents of the foregoing application is incorporated herein by reference in its entirety.

BACKGROUND

The present invention relates to compositions and, in particular, antireflective coating compositions for use in microelectronic application Compositions of the invention comprise a crosslinker of Formula (I). Preferred compositions of the invention are used with an overcoated photoresist composition and may be referred to an bottom antireflective compositions or "BARCs".

Photoresists are photosensitive films used for the transfer of images to a substrate. A coating layer of a photoresist is formed on a substrate and the photoresist layer is then exposed through a photomask to a source of activating radiation. Following exposure, the photoresist is developed to provide a relief image that permits selective processing of a substrate.

Reflection of activating radiation used to expose a photoresist often poses limits on resolution of the image patterned in the photoresist layer. Reflection of radiation from the substrate/photoresist interface can produce spatial variations in the radiation intensity in the photoresist, resulting in non-uniform photoresist linewidth upon development. Radiation also can scatter from the substrate/photoresist interface into regions of the photoresist where exposure is non-intended, again resulting in linewidth variations.

One approach used to reduce the problem of reflected radiation has been the use of a radiation absorbing layer interposed between the substrate surface and the photoresist coating layer. See U.S. Published Applications 2007026458; 2010029556; and 2010009289; U.S. Pat. Nos. 8,334,338; 8,142,988; 7,691,556; 7,638,262; and 7,416,821; and WO2014185335.

For many high performance lithographic applications, particular antireflective compositions are utilized in order to provide the desired performance properties, such as optimal absorption properties and coating characteristics. See, for instance, the above-mentioned patent documents. Nevertheless, electronic device manufacturers continually seek increased resolution of a photoresist image patterned over antireflective coating layers and in turn demand ever-increasing performance from an antireflective composition.

It thus would be desirable to have new antireflective compositions for use with an overcoated photoresist. It would be particularly desirable to have new antireflective compositions that exhibit enhanced performance and could provide increased resolution of an image patterned into an overcoated photoresist.

SUMMARY

We now provide new coating compositions that can be used with overcoated photoresist compositions. In preferred aspects, coating compositions of the invention can function as an effective antireflective layer for an overcoated resist layer.

In a preferred aspect, organic coating compositions, particularly antireflective compositions for use with an overcoated photoresist, are provided that comprise a crosslinker component that is resistant to sublimination from a coating layer as may occur during thermal treatment of a coating layer of the composition.

More particularly, coating compositions are provided that comprise: 1) a resin; and 2) a crosslinker that prior to reaction with the resin comprises a structure of Formula (I):

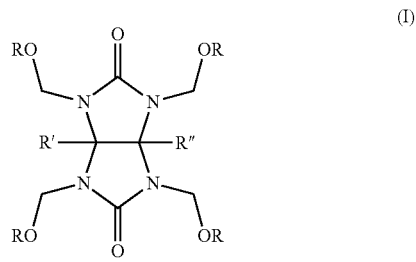

wherein in Formula (I):
each R is independently selected from hydrogen, optionally substituted alkyl, optionally substituted heteroalkyl, optionally substituted carbocyclic aryl, or optionally substituted heteroaryl,
with at least one R group being other than hydrogen;
R' and R" are each independently selected from hydrogen, optionally substituted alkyl or optionally substituted heteroalkyl, optionally substituted carbocyclic aryl, or optionally substituted heteroaryl.

In preferred aspects, at least two of the R groups are the same or different non-hydrogen groups, including where three of four of the R groups are the same or different non-hydrogen groups.

As referred to herein, the crosslinker "prior to reaction with the resin" means prior to thermal-induced hardening or other reaction of the crosslinker and resin components of a coating composition such as during lithographic processing where a coating layer of the composition containing the resin and crosslinker of Formula (I) will be heated in excess of 100° C. for 30 seconds or more.

In preferred aspects, the crosslinker of Formula (I) above has a molecular weight of at least 300, 400, 500, 600, 700, 800, 900 or 1000 daltons. In certain aspects the crosslinker has a molecular weight of less than 1500 daltons. In certain aspects the crosslinker has a molecular weight of between 400 or 500 daltons and 1500 daltons.

In addition preferred aspects, the crosslinker of Formula (I) is thermally stable or resistant, e.g., preferred crosslinkers have a degradation temperature of greater than 250° C. As referred to herein, the degradation temperature of a crosslinker material is defined as determined by the following protocol as defined in Example 11 which follows.

In particularly preferred aspects, such thermally stable crosslinkers (e.g. having a degradation temperature of greater than 250° C.), also function effectively to crosslinker an antireflective composition coating layer, i.e. a coating layer of a composition as disclosed herein that comprises the crosslinker will harden to prevent undesired intermixing with a subsequently applied fluid photoresist composition after heating the antireflective composition layer at 175° C. for 60 seconds.

For antireflective applications, underlying compositions of the invention also preferably contain a component that comprises chromophore groups that can absorb undesired radiation used to expose the overcoated resist layer from reflecting back into the resist layer. The resin or crosslinker may comprise such chromophore groups, or a coating composition may comprise a further component that comprises suitable chromophore groups.

In use with an overcoated photoresist, a coating composition may be applied on a substrate such as a semiconductor wafer which may have one or more organic or inorganic coating layers thereon. The applied coating layer may be optionally thermally treated prior to overcoating with a photoresist layer. Such thermal treatment may cause hardening including crosslinking of the coating composition layer. Such crosslinking may include hardening and/or covalent-bonding forming reactions between one or more composition components and can modulate water contact angle of the coating composition layer.

Thereafter, a photoresist composition may be applied over the coating composition layer followed by imaging of the applied photoresist composition layer with patterned activating radiation and the imaged photoresist composition layer is developed to provide a photoresist relief image.

A variety of photoresists may be used in combination (i.e. overcoated) with a coating composition of the invention. Preferred photoresists for use with the underlying coating compositions of the invention are chemically-amplified resists, especially negative-tone photoresists that contain one or more photoactive compounds and a resin component that contains units that undergo a deblocking or cleavage reaction in the presence of photogenerated acid.

In preferred aspects, the photoresist composition is designed for a negative-tone resist where the light-exposed regions remains after development process, but positive tone development can be also employed to remove the exposed portions of the photoresist layer.

The invention further provides methods for forming a photoresist relief image and novel articles of manufacture comprising substrates (such as a microelectronic wafer substrate) coated with a coating composition of the invention alone or in combination with a photoresist composition. Crosslinker materials of Formula (I) are also provided.

Other aspects of the invention are disclosed infra.

DETAILED DESCRIPTION

As discussed above, organic coating compositions, particularly antireflective compositions for use with an overcoated photoresist, are provided that comprise a crosslinker component that is resistant to sublimination from a coating layer as may occur during thermal treatment of a coating layer of the coating composition.

Without being bound by any theory, it is believed that one or more components of an underlying coating composition can migrate out of an applied coating layer during lithographic processing. In particular, it is believed that during thermal processing of an applied coating composition to crosslink or otherwise harden the coating layer one or more composition components can sublime or otherwise migrate from the coating layer. Such sublimed materials can compromise lithographic performance in a variety of ways, including by depositing on a subsequently applied photoresist coating layer.

As discussed above, we provide coating compositions that comprise:
1) a resin; and
2) a crosslinker that prior to reaction with the resin comprises a structure of Formula (I):

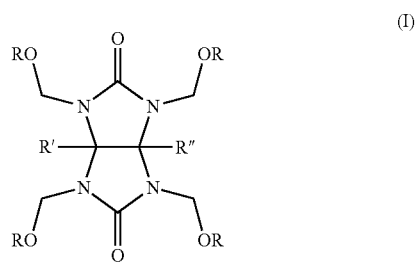

wherein in Formula (I):
each R is independently selected from hydrogen, optionally substituted alkyl, optionally substituted heteroalkyl, optionally substituted carbocyclic aryl, or optionally substituted heteroaryl,
with at least one R being other than hydrogen;
R' and R" are each independently selected from hydrogen, optionally substituted alkyl or optionally substituted heteroalkyl, optionally substituted carbocyclic aryl, or optionally substituted heteroaryl.

In crosslinkers of Formula (I), preferred R groups include optionally substituted alkyl having 1 to 20 carbon atoms, more typically 1 to 12 or 15 carbon atoms; optionally substituted heteroalkyl having one or more N, O or S atoms and 1 to 20 carbon atoms, more typically 1 to 12 or 15 carbon atoms, optionally substituted carbocyclic aryl such as optionally substituted phenyl, napthyl or anthracenyl, or optionally substituted heteroaromatic.

Particularly preferred R groups will contain a total of at least 4, 5 or 6 carbon or hetero (N, O, and/or S) atoms. For instance, specifically preferred R group include those that comprise an optionally substituted carbon alicyclic such as optionally substituted cyclohexyl.

It is also generally preferred that a crosslinker of Formula (I) contain at least two R groups that are the same or different non-hydrogen substituents. Also preferred are crosslinkers of Formula (I) that contain three or four R groups that are the same or different non-hydrogen substituents.

Preferably, if a crosslinker of Formula (I) contains a single R group, the coating composition containing such crosslinker also preferably will contain an acid or acid source such as thermal acid generator compound to promote reaction of the coating composition.

As referred to herein, suitable heteroalkyl include optionally substituted C1-20alkoxy, optionally substituted alkylthio preferably having 1 to about 20 carbon atoms; optionally substituted alkylsulfinyl preferably 1 to about 20 carbon atoms; optionally substituted alkylsulfonyl preferably having 1 to about 20 carbon atoms; and optionally substituted alkylamine preferably having 1 to about 20 carbon atoms.

As referred to herein, the term "carbon alicyclic group" means each ring member of the non-aromatic group is carbon. The carbon alicyclic group can have one or more endocyclic carbon-carbon double bonds, provided the ring is not aromatic. The term optionally substituted "cycloalkyl group" means each ring member of the non-aromatic group is carbon and the carbon ring does not have any endocyclic carbon-carbon double bonds. For instance, cyclohexyl, cyclopentyl and adamantyl are cycloalkyl groups as well as carbon alicyclic groups. Carbon alicyclic groups and cycloalkyl groups may comprise one ring or multiple (e.g. 2, 3, 4 or more) bridged, fused or otherwise covalently linked rings.

As referred to herein, a "heteroaryl" group includes an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Examples of heteroaryl groups include pyridyl, furyl or furanyl, imidazolyl, benzimidazolyl, pyrimidinyl, thiophenyl or thienyl, quinolinyl, indolyl, thiazolyl, and the like.

Various materials and substituents (including groups A, B, X and Y of Formula (I) above) that are "optionally substituted" may be suitably substituted at one or more available positions by e.g. halogen (F, Cl, Br, I); nitro; hydroxy; amino; alkyl such as $C_{1-8}$ alkyl; alkenyl such as $C_{2-8}$ alkenyl; alkylamino such as $C_{1-8}$ alkylamino; carbocyclic aryl such as phenyl, naphthyl, anthracenyl, etc; and the like.

In generally preferred aspects, the resin and crosslinker components of a coating composition prior to thermal treatment are distinct and separate materials, i.e. the resin component and crosslinker component are not covalently linked. In certain other embodiments, the crosslinker component can be linked to the resin component, for example covalently tethered as a pendant group.

A variety of resins may serve as the resin components of an underlying coating composition.

Particularly preferred resins of coating compositions of the invention may comprise polyester linkages. Polyester resins can be readily prepared by reaction of one or more polyol reagents with one or more carboxy-containing (such as a carboxylic acid, ester, anhydride, etc.) compounds. Suitable polyol reagents include diols, glycerols and triols such as e.g. diols such as diol is ethylene glycol, 1,2-propylene glycol, 1,3-propylene glycol, butane diol, pentane diol, cyclobutyl diol, cyclopentyl diol, cyclohexyl diol, dimethylolcyclohexane, and triols such as glycerol, trimethylolethane, trimethylolpropane and the like.

Preferred polyester resins for use in an antireflective composition of the invention are also disclosed in U.S. Pat. No. 8,501,383; U.S. 2011/0033801; and U.S. Pat. No. 7,163, 751. As disclosed in those patent documents, resins that contain ester repeat units (polyester) may be suitably provided by polymerization of a carboxy-containing compound (such as a carboxylic acid, ester, anhydride, etc.) and a hydroxy-containing compound, preferably a compound having multiple hydroxy groups such as a glycol, e.g. ethylene glycol or propylene glycol, or glycerol, or other diols, triols, tetraols and the like. In certain aspects, preferably, an ester functionality is present as a component of, or within, the polymer backbone rather than as a pendant or side chain unit. Ester moieties also may be present as a pendant group, but preferably the polymer also contains an ester functionality along the polymer backbone. Also preferred is where the ester repeat unit comprises aromatic substitution, such as optionally substituted carbocyclic aryl groups e.g. optionally substituted phenyl, naphthyl or anthracenyl substitution, either as a side chain or more preferably along the polymer backbone.

Resins of coating compositions of the invention may comprise a variety of additional groups such as cyanurate groups, as disclosed in U.S. Pat. Nos. 6,852,421 and 8,501, 383.

Particularly preferred matrix resins of coating compositions of the invention may comprise one or more one or more cyanurate groups and polyester linkages.

As discussed, for antireflective applications, suitably one or more of the compounds reacted to form the resin comprise a moiety that can function as a chromophore to absorb radiation employed to expose an overcoated photoresist coating layer. For example, a phthalate compound (e.g. a phthalic acid or dialkyl phthalate (i.e. di-ester such as each ester having 1-6 carbon atoms, preferably a di-methyl or ethyl phthalate) may be polymerized with an aromatic or non-aromatic polyol and optionally other reactive compounds to provide a polyester particularly useful in a coating composition employed with a photoresist imaged at sub-200 nm wavelengths such as 193 nm. An isocyanurate compound also may be polymerized with one or more polyols to provide a resin useful in the present underlying coating compositions. Resins to be used in compositions with an overcoated photoresist imaged at sub-300 nm wavelengths or sub-200 nm wavelengths such as 248 nm or 193 nm, a naphthyl compound may be polymerized, such as a naphthyl compound containing one or two or more carboxyl substituents e.g. dialkyl particularly di-$C_{1-6}$alkyl naphthalenedicarboxylate. Reactive anthracene compounds also are preferred, e.g. an anthracene compound having one or more carboxy or ester groups, such as one or more methyl ester or ethyl ester groups.

The compound that contains a chromophore unit also may contain one or preferably two or more hydroxy groups and be reacted with a carboxyl-containing compound. For example, a phenyl compound or anthracene compound having one, two or more hydroxyl groups may be reacted with a carboxyl-containing compound.

Additionally, underlying coating compositions that are employed for antireflective purposes may contain a material that contains chromophore units that is separate from a resin component that provides water contact angle modulation (e.g. a resin that contains photoacid-labile groups and/or base-reactive groups. For instance, the coating composition may comprise a polymeric or non-polymeric compound that contains phenyl, anthracene, naphthyl, etc. units. It is often preferred, however, that the one or more resins that provide water contact angle modulation also contain chromophore moieties.

Preferably resins of underlying coating compositions of the invention will have a weight average molecular weight (Mw) of about 1,000 to about 10,000,000 daltons, more typically about 2,000 to about 100,000 daltons, and a number average molecular weight (Mn) of about 500 to about 1,000,000 daltons. Molecular weights (either Mw or Mn) of the resins of compositions of the invention are suitably determined by gel permeation chromatography.

The resin component will be the major solids component of an underlying coating composition in many preferred embodiments. For instance, the resin suitably may be present from 50 to 99.9 weight percent based on total solid content of a coating composition, more typically from 80 to 95 weight percent based total solid content of a coating composition. As referred to herein, solids of a coating composition refer to all materials of the coating composition except solvent carrier.

In certain embodiments, a coating composition of the invention may comprise a crosslinker in addition to a crosslinker of Formula (I). For example, coating compositions may include amine-based crosslinkers such as melamine materials, including melamine resins such as manufactured by Cytec Industries and sold under the tradename of Cymel 300, 301, 303, 350, 370, 380, 1116 and 1130; glycolurils including those glycolurils available from Cytec Industries; and benzoquanamines and urea-based materials including resins such as the benzoquanamine resins available from Cytec Industries under the name Cymel 1123 and 1125, and urea resins available from Cytec Industries under the names of Powderlink 1174 and 1196. In addition to being commercially available, such amine-based resins may be prepared e.g. by the reaction of acrylamide or methacrylamide copolymers with formaldehyde in an alcohol-containing solution, or alternatively by the copolymerization of N-alkoxymethyl acrylamide or methacrylamide with other suitable monomers.

A crosslinker component of a coating composition of the invention in general is present in an amount of between about 5 and 50 weight percent of total solids (all components except solvent carrier) of the coating composition, more typically in an amount of about 5 to 25 weight percent total solids.

Particularly preferred coating compositions of the invention also may contain a thermal acid generator compound. Thermal-induced crosslinking of the coating composition by activation of the thermal acid generator is generally preferred.

Suitable thermal acid generator compounds for use in a coating composition include ionic or substantially neutral thermal acid generators, e.g. an ammonium arenesulfonate salt (e.g. toluene sulfonic acid ammonium salt), for catalyzing or promoting crosslinking during curing of an antireflective composition coating layer. Typically one or more thermal acid generators are present in an coating composition in a concentration from about 0.1 to 10 percent by weight of the total of the dry components of the composition (all components except solvent carrier), more preferably about 0.5 to 2 percent by weight of the total dry components.

Coating compositions of the invention, particularly for reflection control applications, also may contain additional dye compounds that absorb radiation used to expose an overcoated photoresist layer. Other optional additives include surface leveling agents, for example, the leveling agent available under the tradename Silwet 7604, or the surfactant FC 171 or FC 431 available from the 3M Company.

Underlying coating compositions of the invention also may contain other materials such as a photoacid generator, including a photoacid generator as discussed for use with an overcoated photoresist composition. See U.S. Pat. No. 6,261,743 for a discussion of such use of a photoacid generator in an antireflective composition.

To make a liquid coating composition of the invention, the components of the coating composition are dissolved in a suitable solvent such as, for example, one or more oxyisobutyric acid esters particularly methyl-2-hydroxyisobutyrate, ethyl lactate or one or more of the glycol ethers such as 2-methoxyethyl ether (diglyme), ethylene glycol monomethyl ether, and propylene glycol monomethyl ether; solvents that have both ether and hydroxy moieties such as methoxy butanol, ethoxy butanol, methoxy propanol, and ethoxy propanol; methyl 2-hydroxyisobutyrate; esters such as methyl cellosolve acetate, ethyl cellosolve acetate, propylene glycol monomethyl ether acetate, dipropylene glycol monomethyl ether acetate and other solvents such as dibasic esters, propylene carbonate and gamma-butyro lactone. The concentration of the dry components in the solvent will depend on several factors such as the method of application. In general, the solid content of an underlying coating composition varies from about 0.5 to 20 weight percent of the total weight of the coating composition, preferably the solid content varies from about 0.5 to 10 weight of the coating composition.

Exemplary Photoresist Systems

Photoresists for use with an underlying coating composition typically comprise a polymer and one or more acid generators. Generally preferred are positive-tone resists and the resist polymer has functional groups that impart alkaline aqueous solubility to the resist composition. For example, preferred are polymers that comprise polar functional groups such as hydroxyl or carboxylate, or acid-labile groups that can liberate such polar moieties upon lithographic processing. Preferably the polymer is used in a resist composition in an amount sufficient to render the resist developable with an aqueous alkaline solution.

Acid generators are also suitably used with polymers that comprise repeat units containing aromatic groups, such as optionally substituted phenyl including phenol, optionally substituted naphthyl, and optionally substituted anthracene. Optionally substituted phenyl (including phenol) containing polymers are particularly suitable for many resist systems, including those imaged with EUV and e-beam radiation. For positive-acting resists, the polymer also preferably contains one or more repeat units that comprise acid-labile groups. For example, in the case of polymers containing optionally substituted phenyl or other aromatic groups, a polymer may comprise repeat units that contain one or more acid-labile moieties such as a polymer that is formed by polymerization of monomers of an acrylate or methacrylate compound with acid-labile ester (e.g. t-butyl acrylate or t-butyl methacrylate). Such monomers may be copolymerized with one or more other monomers that comprise aromatic group(s) such as optionally phenyl, e.g. a styrene or vinyl phenol monomer.

Preferred monomers used for the formation of such polymers include: an acid-labile monomer having the following formula (V), a lactone-containing monomer of the following formula (VI), a base-soluble monomer of the following formula (VII) for adjusting dissolution rate in alkaline developer, and an acid-generating monomer of the following formula (VIII), or a combination comprising at least one of the foregoing monomers:

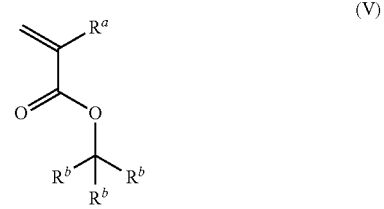

(V)

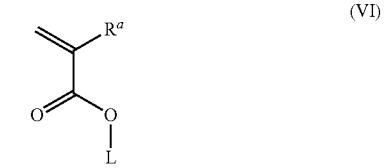

(VI)

(VII)

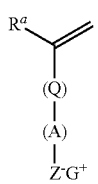

wherein each $R^a$ is independently H, F, —CN, $C_{1-10}$ alkyl, or $C_{1-10}$ fluoroalkyl. In the acid-deprotectable monomer of formula (V), $R^b$ is independently $C_{1-20}$ alkyl, $C_{3-20}$ cycloalkyl, $C_{6-20}$ aryl, or $C_{7-20}$ aralkyl, and each $R^b$ is separate or at least one $R^b$ is bonded to an adjacent $R^b$ to form a cyclic structure. In lactone-containing monomer of formula (VI), L is a monocyclic, polycyclic, or fused polycyclic $C_{4-20}$ lactone-containing group. In the base solubilizing monomer of formula (VII), W is a halogenated or non-halogenated, aromatic or non-aromatic $C_{2-50}$ hydroxyl-containing organic group having a pKa of less than or equal to 12. In the acid generating monomer of formula (VIII), Q is ester-containing or non-ester containing and fluorinated or non-fluorinated and is $C_{1-20}$ alkyl, $C_{3-20}$ cycloalkyl, $C_{6-20}$ aryl, or $C_{7-20}$ aralkyl group, A is ester-containing or non-ester-containing and fluorinated or non-fluorinated, and is $C_{1-20}$ alkyl, $C_{3-20}$ cycloalkyl, $C_{6-20}$ aryl, or $C_{7-20}$ aralkyl, Z is an anionic moiety comprising carboxylate, sulfonate, an anion of a sulfonamide, or an anion of a sulfonimide, and $G^+$ is a sulfonium or iodonium cation.

Exemplary acid-deprotectable monomers include but are not limited to:

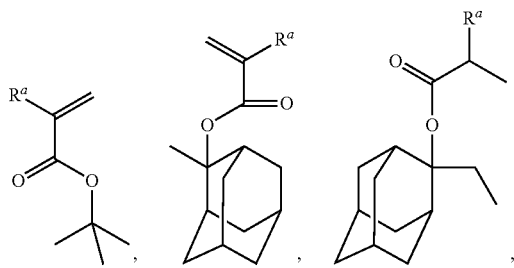

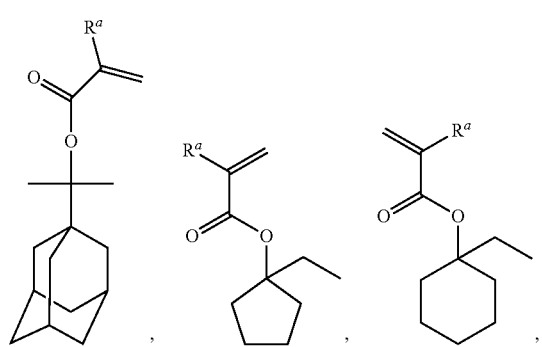

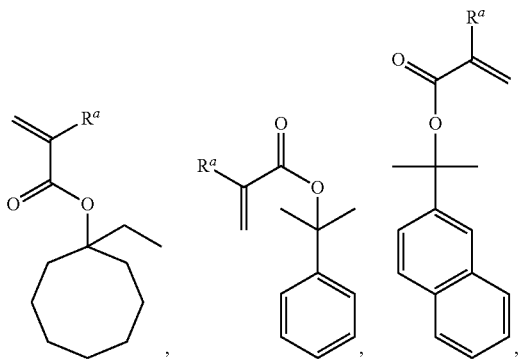

or a combination comprising at least one of the foregoing, wherein $R^a$ is H, F, —CN, $C_{1-6}$ alkyl, or $C_{1-6}$ fluoroalkyl.

Suitable lactone monomers may be of the following formula (IX):

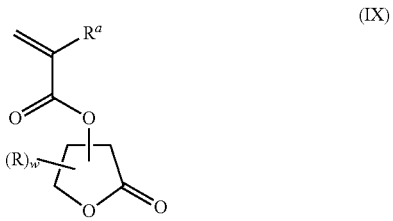

wherein $R^a$ is H, F, —CN, $C_{1-6}$ alkyl, or $C_{1-6}$ fluoroalkyl, R is a $C_{1-10}$ alkyl, cycloalkyl, or heterocycloalkyl, and w is an integer of 0 to 5. In formula (IX), R is attached directly to the lactone ring or commonly attached to the lactone ring and/or one or more R groups, and the ester moiety is attached to the lactone ring directly, or indirectly through R.

Exemplary lactone-containing monomers include:

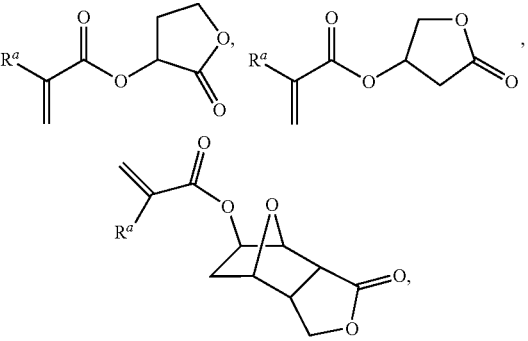

or a combination comprising at least one of the foregoing monomers, wherein $R^a$ is H, F, —CN, $C_{1-10}$ alkyl, or $C_{1-10}$ fluoroalkyl.

Suitable base-soluble monomers may be of the following formula (X):

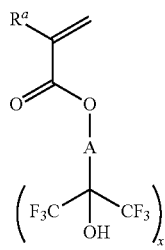

(X)

wherein each $R^a$ is independently H, F, —CN, $C_{1-10}$ alkyl, or $C_{1-10}$ fluoroalkyl, A is a hydroxyl-containing or non-hydroxyl containing, ester-containing or non ester-containing, fluorinated or non-fluorinated $C_{1-10}$ alkylene, $C_{3-20}$ cycloalkylene, $C_{6-20}$ arylene, or $C_{7-20}$ aralkylene, and x is an integer of from 0 to 4, wherein when x is 0, A is a hydroxyl-containing $C_{6-20}$ arylene.

Exemplary base soluble monomers include those having the following structures:

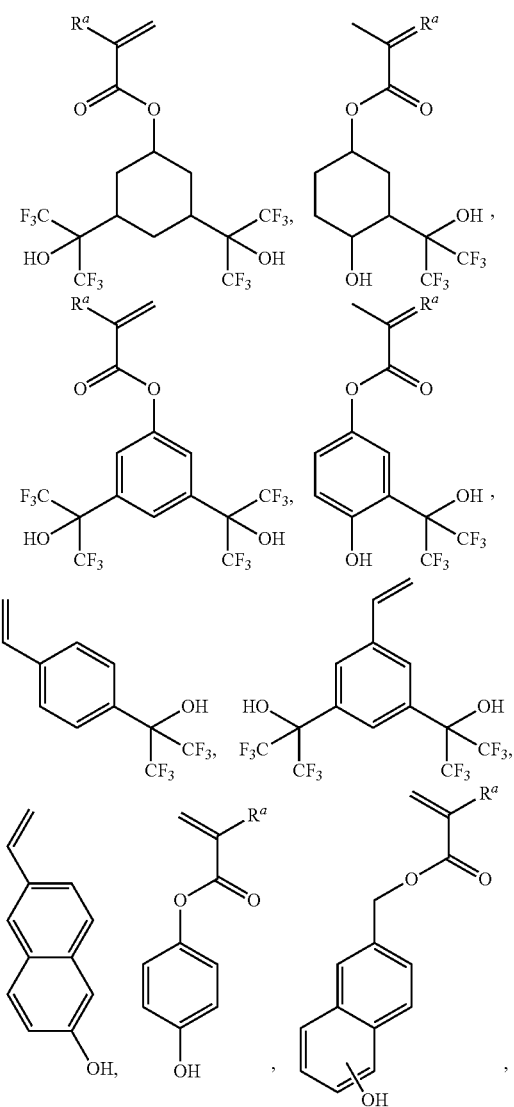

or a combination comprising at least one of the foregoing, wherein $R^a$ is H, F, —CN, $C_{1-6}$ alkyl, or $C_{1-6}$ fluoroalkyl.

Preferred acid generating monomers include those of the formulae (XI) or (XII):

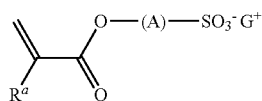

(XI)

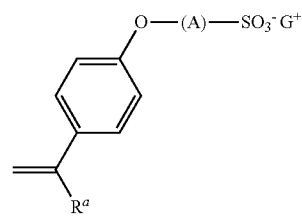

(XII)

wherein each $R^a$ is independently H, F, —CN, $C_{1-6}$ alkyl, or $C_{1-6}$ fluoroalkyl, A is a fluorine-substituted $C_{1-30}$ alkylene group, a fluorine-substituted $C_{3-30}$ cycloalkylene group, a fluorine-substituted $C_{6-30}$ arylene group, or a fluorine-substituted $C_{7-30}$ alkylene-arylene group, and $G^+$ is a sulfonium or iodonium cation.

Preferably, in formulas (XI) and (XII), A is a —[$C(R^1)_2)_xC(=O)O]_b$—$C((R^2)_2)_y(CF_2)_z$— group, or an o-, m- or p-substituted —$C_6F_4$— group, where each $R^1$ and $R^2$ are each independently H, F, —CN, $C_{1-6}$ fluoroalkyl, or $C_{1-6}$ alkyl, b is 0 or 1, x is an integer of 1 to 10, y and z are independently integers of from 0 to 10, and the sum of y+z is at least 1.

Exemplary preferred acid generating monomers include:

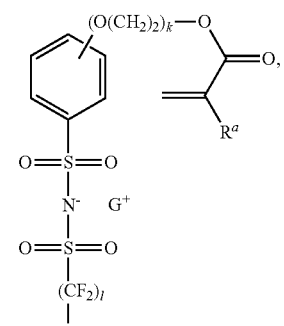

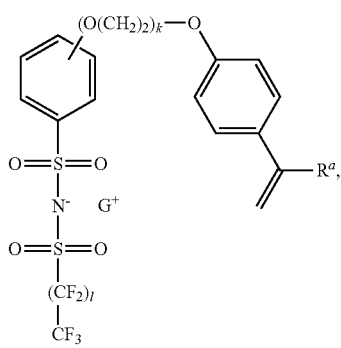

-continued

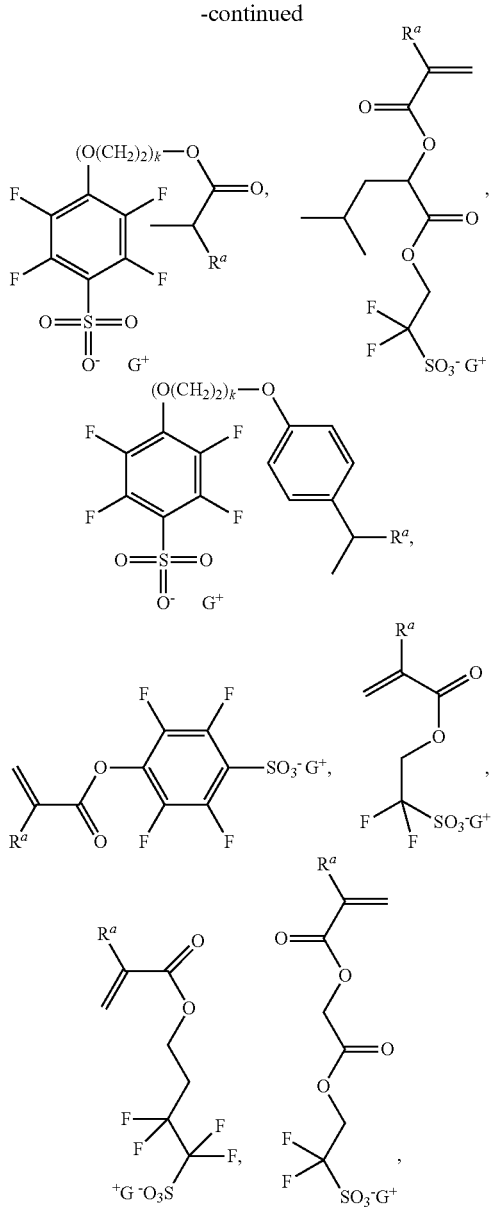

or a combination comprising at least one of the foregoing, where each $R^a$ is independently H, F, —CN, $C_{1-6}$ alkyl, or $C_{1-6}$ fluoroalkyl, k is suitably an integer of from 0 to 5; and $G^+$ is a sulfonium or iodonium cation. $G^+$ as referred to herein throughout the various formulae may be an acid generator as disclosed herein and comprise an oxo-dioxolane moiety and/or an oxo-dioxane moiety.

Preferred acid-generating monomers may include sulfonium or iodonium cation. Preferably, in formula (IV), $G^+$ is of the formula (XIII):

(XIII)

wherein X is S or I, each $R^0$ is halogenated or non-halogenated and is independently $C_{1-30}$ alkyl group; a polycyclic or monocyclic $C_{3-30}$ cycloalkyl group; a polycyclic or monocyclic $C_{4-30}$ aryl group; or a combination comprising at least one of the foregoing, wherein when X is S, one of the $R^0$ groups is optionally attached to one adjacent $R^0$ group by a single bond, and a is 2 or 3, wherein when X is I, a is 2, or when X is S, a is 3.

Exemplary acid generating monomers include those having the formulas:

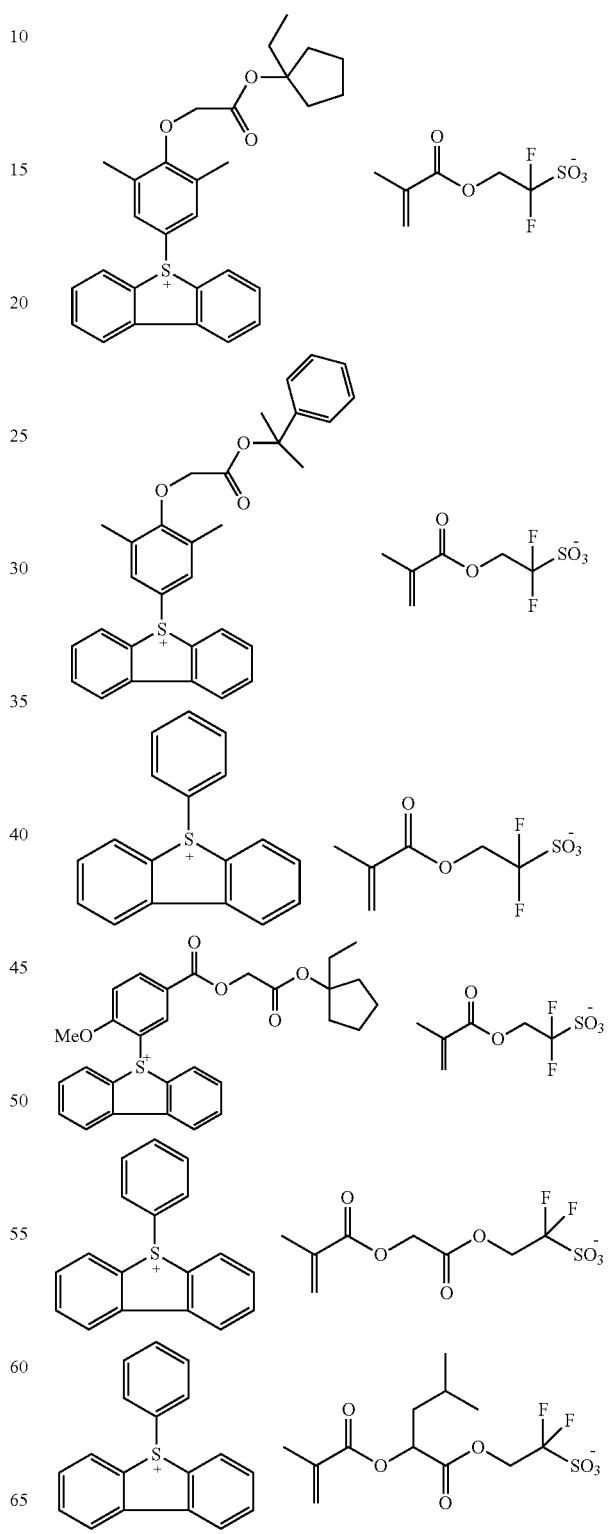

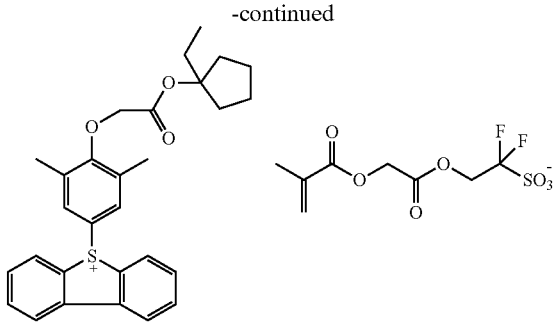

Specifically suitable polymers that have acid-labile deblocking groups for use in a positive-acting chemically-amplified photoresist of the invention have been disclosed in European Patent Application 0829766A2 (polymers with acetal and ketal polymers) and European Patent Application EP0783136A2 (terpolymers and other copolymers including units of 1) styrene; 2) hydroxystyrene; and 3) acid labile groups, particularly alkyl acrylate acid labile groups.

Additional preferred resins for use in photoresists to be imaged at sub-200 nm, such as at 193 nm, comprises units of the following general formulae (I), (II) and (III):

Preferred resins for use in photoresists to be imaged at sub-200 nm, such as at 193 nm, comprise units of the following general formulae (I), (II) and (III):

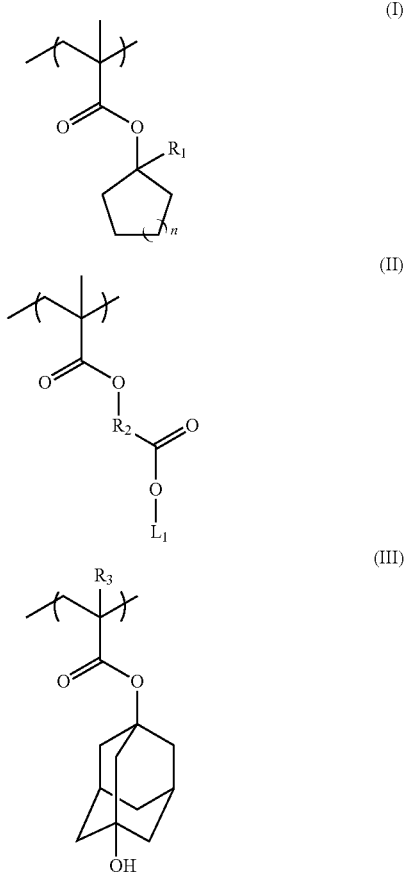

wherein: $R_1$ is a $(C_1-C_3)$alkyl group; $R_2$ is a $(C_1-C_3)$alkylene group; $L_1$ is a lactone group; and n is 1 or 2.

Polymers for use in photoresists of the invention may suitably vary widely in molecular weight and polydisperity. Suitable polymers include those that have an $M_w$ of from about 1,000 to about 50,000, more typically about 2,000 to about 30,000 with a molecular weight distribution of about 3 or less, more typically a molecular weight distribution of about 2 or less.

Preferred negative-acting compositions of the invention comprise a mixture of materials that will cure, crosslink or harden upon exposure to acid, and two or more acid generators as disclosed herein. Preferred negative acting compositions comprise a polymer binder such as a phenolic or non-aromatic polymer, a crosslinker component and a photoactive component of the invention. Such compositions and the use thereof have been disclosed in European Patent Applications 0164248 and U.S. Pat. No. 5,128,232 to Thackeray et al. Preferred phenolic polymers for use as the polymer binder component include novolaks and poly(vinylphenol)s such as those discussed above. Preferred crosslinkers include amine-based materials, including melamine, glycolurils, benzoguanamine-based materials and urea-based materials. Melamine-formaldehyde polymers are often particularly suitable. Such crosslinkers are commercially available, e.g. the melamine polymers, glycoluril polymers, urea-based polymer and benzoguanamine polymers, such as those sold by Cytec under tradenames Cymel 301, 303, 1170, 1171, 1172, 1123 and 1125 and Beetle 60, 65 and 80.

Particularly preferred photoresists of the invention may be used in immersion lithography applications. See, for example, U.S. Pat. No. 7,968,268 to Rohm and Haas Electronic Materials for a discussion of preferred immersion lithography photoresists and methods.

Photoresists of the invention also may comprise a single acid generator or a mixture of distinct acid generators, typically a mixture of 2 or 3 different acid generators, more typically a mixture that consists of a total of 2 distinct acid generators. The photoresist composition comprises an acid generator employed in an amount sufficient to generate a latent image in a coating layer of the composition upon exposure to activating radiation. For example, the acid generator will suitably be present in an amount of from 1 to 20 wt % based on total solids of the photoresist composition.

Suitable acid generators are known in the art of chemically amplified photoresists and include, for example: onium salts, for example, triphenylsulfonium trifluoromethanesulfonate, (p-tert-butoxyphenyl)diphenylsulfonium trifluoromethanesulfonate, tris(p-tert-butoxyphenyl)sulfonium trifluoromethanesulfonate, triphenylsulfonium p-toluenesulfonate; nitrobenzyl derivatives, for example, 2-nitrobenzyl-p-toluenesulfonate, 2,6-dinitrobenzyl-p-toluenesulfonate, and 2,4-dinitrobenzyl-p-toluenesulfonate; sulfonic acid esters, for example, 1,2,3-tris(methanesulfonyloxy)benzene, 1,2,3-tris(trifluoromethanesulfonyloxy)benzene, and 1,2,3-tris(p-toluenesulfonyloxy)benzene; diazomethane derivatives, for example, bis(benzenesulfonyl)diazomethane, bis(p-toluenesulfonyl)diazomethane; glyoxime derivatives, for example, bis-O-(p-toluenesulfonyl)-α-dimethylglyoxime, and bis-O-(n-butanesulfonyl)-α-dimethylglyoxime; sulfonic acid ester derivatives of an N-hydroxyimide compound, for example, N-hydroxysuccinimide methanesulfonic acid ester, N-hydroxysuccinimide trifluoromethanesulfonic acid ester; and halogen-containing triazine compounds, for example, 2-(4-methoxyphenyl)-4,6-bis(trichloromethyl)-1,3,5-triazine, and 2-(4-methoxynaphthyl)-4,6-bis(trichloromethyl)-1,3,5-triazine.

As referred to herein, acid generators can produce an acid when exposed to activating radiation, such as EUV radiation, e-beam radiation, 193 nm wavelength radiation or other radiation sources. Acid generator compounds as referred to herein also may be referred to as photoacid generator compounds.

Photoresists of the invention also may contain other materials. For example, other optional additives include actinic and contrast dyes, anti-striation agents, plasticizers, speed enhancers and sensitizers. Such optional additives typically will be present in minor concentration in a photoresist composition.

Alternatively, or in addition, other additives may include quenchers that are non-photo-destroyable bases, such as, for example, those based on hydroxides, carboxylates, amines, imines, and amides. Preferably, such quenchers include $C_{1-30}$ organic amines, imines, or amides, or may be a $C_{1-30}$ quaternary ammonium salt of a strong base (e.g., a hydroxide or alkoxide) or a weak base (e.g., a carboxylate). Exemplary quenchers include amines such as tripropylamine, dodecylamine, tris(2-hydroxypropyl)amine, oltetrakis (2-hydroxypropyl)ethylenediamine; aryl amines such as diphenylamine, triphenylamine, aminophenol, and 2-(4-aminophenyl)-2-(4-hydroxyphenyl)propane, a hindered amine such as diazabicycloundecene (DBU) or diazabicy-clononene (DBN), or ionic quenchers including quaternary alkyl ammonium salts such as tetrabutylammonium hydroxide (TBAH) or tetrabutylammonium lactate.

Surfactants include fluorinated and non-fluorinated surfactants, and are preferably non-ionic. Exemplary fluorinated non-ionic surfactants include perfluoro $C_4$ surfactants such as FC-4430 and FC-4432 surfactants, available from 3M Corporation; and fluorodiols such as POLYFOX PF-636, PF-6320, PF-656, and PF-6520 fluorosurfactants from Omnova.

The photoresist further includes a solvent generally suitable for dissolving, dispensing, and coating the components used in a photoresists. Exemplary solvents include anisole, alcohols including ethyl lactate, 1-methoxy-2-propanol, and 1-ethoxy-2 propanol, esters including n-butylacetate, 1-methoxy-2-propyl acetate, methoxyethoxypropionate, ethoxyethoxypropionate, ketones including cyclohexanone and 2-heptanone, and a combination comprising at least one of the foregoing solvents.

Lithographic Processing

In use, a coating composition of the invention is applied as a coating layer to a substrate by any of a variety of methods such as spin coating. The coating composition in general is applied on a substrate with a dried layer thickness of between about 0.02 and 0.5 µm, preferably a dried layer thickness of between about 0.04 and 0.20 µm. The substrate is suitably any substrate used in processes involving photoresists. For example, the substrate can be silicon, silicon dioxide or aluminum-aluminum oxide microelectronic wafers. Gallium arsenide, silicon carbide, ceramic, quartz or copper substrates may also be employed. Substrates for liquid crystal display or other flat panel display applications are also suitably employed, for example glass substrates, indium tin oxide coated substrates and the like. Substrates for optical and optical-electronic devices (e.g. waveguides) also can be employed.

Preferably the applied coating layer is cured before a photoresist composition is applied over the underlying coating composition. Cure conditions will vary with the components of the underlying coating composition. Particularly the cure temperature will depend on the specific acid or acid (thermal) generator that is employed in the coating composition. Typical cure conditions are from about 80° C. to 225° C. for about 0.5 to 5 minutes. Cure conditions preferably render the coating composition coating layer substantially insoluble to the photoresist solvent as well the developer solution to be used.

After such curing, a photoresist is applied above the surface of the applied coating composition. As with application of the bottom coating composition layer(s), the overcoated photoresist can be applied by any standard means such as by spinning, dipping, meniscus or roller coating. Following application, the photoresist coating layer is typically dried by heating to remove solvent preferably until the resist layer is tack free. Optimally, essentially no intermixing of the bottom composition layer and overcoated photoresist layer should occur.

The resist layer is then imaged with activating radiation such as 248 nm, 193 nm or EUV radiation through a mask in a conventional manner. The exposure energy is sufficient to effectively activate the photoactive component of the resist system to produce a patterned image in the resist coating layer. Typically, the exposure energy ranges from about 3 to 300 mJ/cm$^2$ and depending in part upon the exposure tool and the particular resist and resist processing that is employed. The exposed resist layer may be subjected to a post-exposure bake if desired to create or enhance solubility differences between exposed and unexposed regions of a coating layer. For example, negative acid-hardening photoresists typically require post-exposure heating to induce the acid-promoted crosslinking reaction, and many chemically amplified positive-acting resists require post-exposure heating to induce an acid-promoted deprotection reaction. Typically post-exposure bake conditions include temperatures of about 50° C. or greater, more specifically a temperature in the range of from about 50° C. to about 160° C.

The photoresist layer also may be exposed in an immersion lithography system, i.e. where the space between the exposure tool (particularly the projection lens) and the photoresist coated substrate is occupied by an immersion fluid, such as water or water mixed with one or more additives such as cesium sulfate which can provide a fluid of enhanced refractive index. Preferably the immersion fluid (e.g., water) has been treated to avoid bubbles, e.g. water can be degassed to avoid nanobubbles.

References herein to "immersion exposing" or other similar term indicates that exposure is conducted with such a fluid layer (e.g. water or water with additives) interposed between an exposure tool and the coated photoresist composition layer.

The exposed photoresist layer is then treated with a suitable developer capable of selectively removing portions of the film to form a photoresist pattern. In a negative tone development process, unexposed regions of a photoresist layer can be selectively removed by treatment with a suitable nonpolar solvent. See U.S. 2011/0294069 for suitable procedures for negative tone development. Typical nonpolar solvents for negative tone development are organic developers, such as a solvent chosen from ketones, esters, hydrocarbons, and mixtures thereof, e.g. acetone, 2-hexanone, 2-heptanone, methyl acetate, butyl acetate, and tetrahydrofuran. Photoresist materials used in the NTD process preferably form a photoresist layer that can form a negative image with organic solvent developer or a positive image with aqueous base developer such as tetraalkylammonium hydroxide solution. Preferably, the NTD photoresist is based on a polymer having acid sensitive (deprotectable) groups which, when deprotected, form carboxylic acid groups and/or hydroxyl groups.

Alternatively, development of the exposed photoresist layer can be accomplished by treating the exposed layer to a suitable developer capable of selectively removing the exposed portions of the film (where the photoresist is positive tone) or removing the unexposed portions of the film (where the photoresist is crosslinkable in the exposed regions, i.e., negative tone). Preferably, the photoresist is positive tone based on a polymer having acid sensitive (deprotectable) groups which form carboxylic acid groups when deprotected, and the developer is preferably a metal-ion free tetraalkylammonium hydroxide solution, such as, for example, aqueous 0.26 N tetramethylammonium hydroxide. A pattern forms by developing.

The developed substrate may then be selectively processed on those substrate areas bared of photoresist, for example, chemically etching or plating substrate areas bared of photoresist in accordance with procedures well known in the art. Suitable etchants include a hydrofluoric acid etching solution and a plasma gas etch such as an oxygen plasma etch. A plasma gas etch removes the underlying coating layer.

The following non-limiting examples are illustrative of the invention.

Example 1: Preparation of tetra(cyclohexoxymethyl)-3a-butyl-6a-methylglycoluril

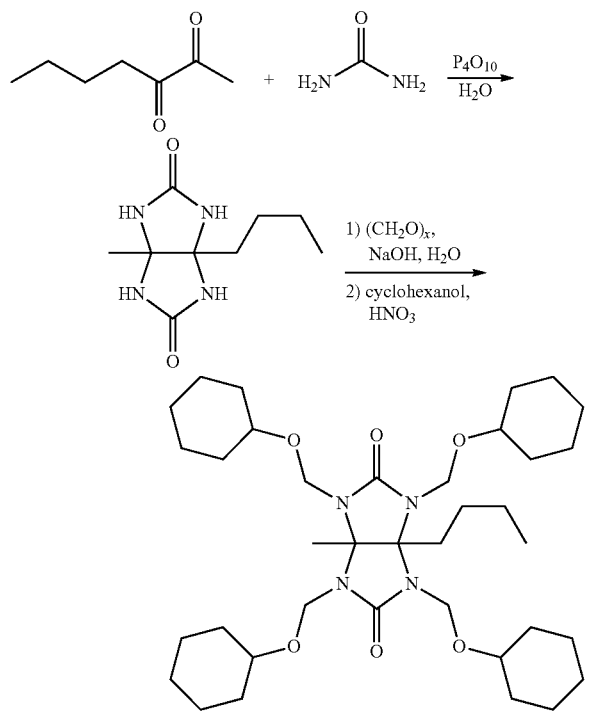

The title compound, tetra(cyclohexoxymethyl)-3a-butyl-6a-methylglycoluril, was prepared as shown in the Scheme immediately above an as follows:
(a) To a 100 mL round-bottom flask equipped with a magnetic stir bar was dissolved 2,3-heptanedione (3.915 g, 30.5 mmol) in water (57 mL). To this solution was charged phosphoric anhydride (4.86 g, 17.1 mmol) and this solution was allowed to stir for 10 minutes. To this resulting clear, colorless solution was charged urea (5.393 g, 89.8 mmol) and the entire reaction mixture was allowed to stir at ambient temperature for 20 minutes. The resulting heterogeneous solution was cooled to ambient temperature and the solid was collected by filtration. The solid was washed with cold water before being dried under high vacuum to give 3a-butyl-6a-methyl-glycoluril as 2.74 g (42% yield) of a white powder. $^1$H NMR (d$_6$-DMSO) δ=7.14 (2H, s), 7.06 (2H, s), 1.59 (2H, m), 1.35 (7H, m), 0.87 (3H, t, J=7.5 Hz) ppm. $^{13}$C NMR (d$_6$-DMSO) δ=160.22, 160.12, 77.83, 76.02, 35.48, 25.19, 22.95, 21.97, 14.34 ppm.

(b) To a 25 mL scintillation vial equipped with a magnetic stir bar was charged 3a-butyl-6a-methyl-glycoluril (1.71 g, 8.1 mmol) and 8 mL of water. To this mixture was charged paraformaldehyde (1.91 g, 63.7 mmol) and 1 mL of 5% NaOH (16%). This mixture was heated to 50° C. and allowed to stir overnight. The clear, homogenous solution was filtered while stir hot and the resulting solution was evaporated to dryness to give a viscous oil that was used in the next step without any further purification.

(c) To a 100 mL round-bottom flask equipped with magnetic stir bar was charged the previous viscous oil, cyclohexanol (20 g, 199.7 mmol), and concentrated nitric acid (4.2 mL, 65.4 mmol). This mixture was heated to 60° C. and held at that temperature overnight while stirring. The resulting mixture was then neutralized with 5% sodium hydroxide (aq) before being extracted with methylene chloride (2×). The combined organic fractions were washed with brine, dried over anhydrous magnesium sulfate, and then concentrated by rotary evaporation to get the crude product mixture which upon sitting at 2° C. overnight yielded tetra(cyclohexoxymethyl)-3a-butyl-6a-methylglycoluril as colorless needles (0.38 g, 7.1% over two steps) that were collected by vacuum filtration. Additional product was collected by a second crystallization to give a total yield of the title compound, tetra(cyclohexoxymethyl)-3a-butyl-6a-methylglycoluril, up to 1.1 gram (20.7% over two steps). $^1$H NMR (d$_6$-DMSO) δ=5.22 (1H, d, J=10 Hz), 5.20 (1H, d, J=10 Hz), 5.01 (1H, d, J=10 Hz), 4.95 (1H, d, J=10 Hz), 3.38 (4H, m) 2.28 (2H, dd, J=7.5, 7.5 Hz), 1.84 (3H, s), 1.73 (6H, m), 1.64 (6H, m), 1.46 (4H, m), 1.39 (4H, m), 1.22-1.11 (20H, m), 0.91 (3H, dd, J=5.0, 5.0 Hz) ppm. 13C NMR (d6-DMSO) 158.04, 75.79, 74.04, 70.82, 70.57, 68.68, 39.72, 35.83, 28.65, 26.37, 25.82, 24.26, 22.53, 17.10, 14.28 ppm. ESI-MS m/z=683 [M+Na]$^+$.

Example 2: Condensation of Tetra(Hydroxymethyl)Glycoluril with Cyclohexanol

To tetra(hydroxymethyl)glycoluril (1.0 eq.) suspended in cyclohexanol (20.0 eq.) is added concentrated nitric acid (4.4 eq.). This mixture is heated to dissolve the glycoluril and then stirred at the elevated temperature until the reaction is completed. The final reaction mixture is cooled to ambient temperature, neutralized with dilute caustic, dried over magnesium sulfate, and then concentrated by rotary evaporation. The final product is isolated by either crystallization from the crude reaction mixture or by purification via column chromatography (EtOAc:Hex) to give the target compound as a white crystalline solid.

Example 3: Coupling of Chloromethyl Cyclohexylether with Glycoluril

To glycoluril (1.0 eq) dissolved in tetrahydrofuran is added chloromethyl cyclohexylether (4.4 eq) and dilute sodium hydroxide (8.8 eq.). This solution is stirred for elevated temperature until complete. The resulting solution is extracted with methylene chloride, dried over magnesium sulfate, and concentrated by rotary evaporation. The final product is isolated by either crystallization or column chromatography (EtOAc:Hex) to give the target compound as a white crystalline solid.

Example 4: Coupling of Cyclohexanol with Tetra(Chloromethyl)Glycoluril

Tetra(chloromethyl)glycoluril (1.0 eq) dissolved in tetrahydrofuran is slowly added to a solution of cyclohexanol (4.4 eq) and sodium hydride (8.8 eq.) in tetrahydrofuran held at 0 C. The resulting reaction mixture is heated to 60 C and allowed to stir overnight. The resulting solution is cooled to 0 C and quenched with careful addition of water. The resulting mixture is extracted with methylene chloride, dried over magnesium sulfate, and concentrated by rotary evaporation. The final product is isolated by either crystallization or column chromatography (EtOAc:Hex) to give the target compound as a white crystalline solid.

Example 5: Coupling of Cyclohexanol with Tetra(Acetoxymethyl)Glycoluril

Tetra(acetoxymethyl)glycoluril (1.0 eq) dissolved in tetrahydrofuran is slowly added to a solution of cyclohexanol (4.4 eq) and sodium hydride (8.8 eq.) in tetrahydrofuran held at 0° C. The resulting reaction mixture is heated to 60° C. and allowed to stir overnight. The resulting solution is cooled to 0° C. and quenched with careful addition of water. The resulting mixture is extracted with methylene chloride, dried over magnesium sulfate, and concentrated by rotary evaporation. The final product is isolated by either crystallization or column chromatography (EtOAc:Hex) to give the target compound as a white crystalline solid.

Example 6: Synthesis of Tetra(n-Hexyl)Glycoluril

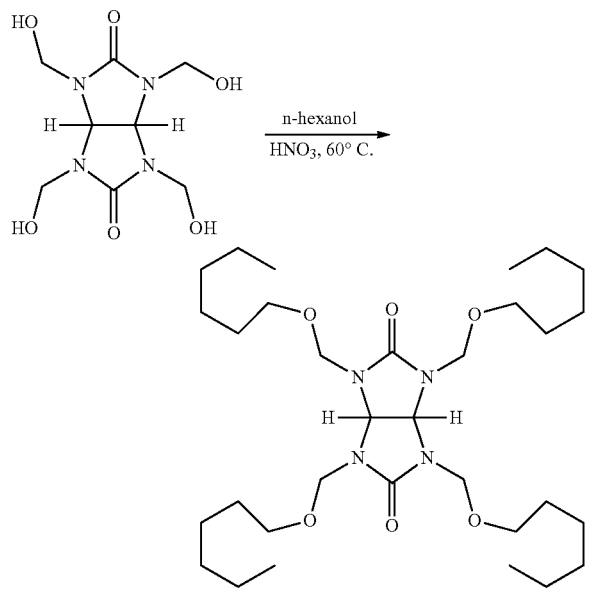

1,3,4,6-tetrakis(hydroxymethyl)tetrahydroimidazo[4,5-d]imidazole-2,5(1H,3H)-dione (1 g, 3.8 mmol) in 2 ml of DMSO was dissolved. Then, 0.15 ml nitric acid (65%) and n-hexylalcohol (9.5 ml, 76.3 mmol) were added to the solution and the mixture was heated at 60° C. for 16 hours. After the reaction was over, the reaction liquid was cooled and 1N NaOH was added around pH 7. Around 100 ml ethyl acetate was used to extract with mixture and the organic phase was washed by saturated NaCl(aq) solution for 2 times. After being dried by Na2SO4, the solvent was removed. The crude compound was purified by flash chromatography (Heptane/EtOAc). The product was obtained colorless viscous oil in 0.15 g, yield (%) $^1$H NMR (600 MHz, DMSO-d6): δ ppm) 5.50 (s, 2H), 4.73 (m, 8H), 3.36 (m, 8H), 1.46 (m, 8H), 1.24 (m, 26H), 0.85 (t, 12H).

Example 7: Synthesis of Tetra(n-Butyl) Glycoluril

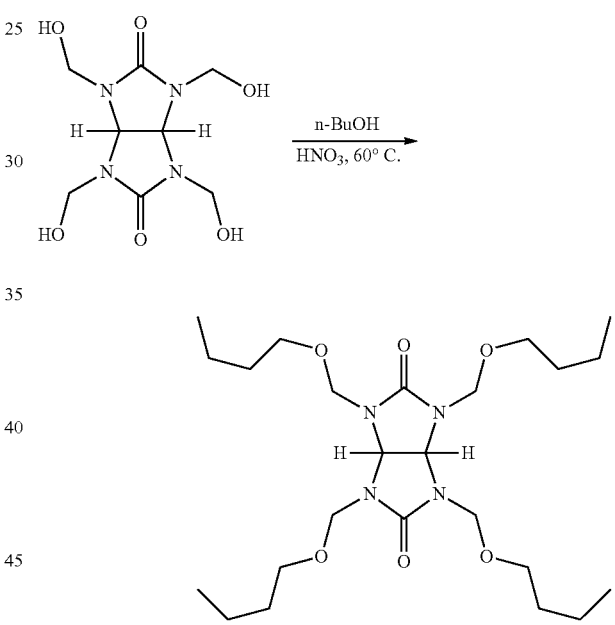

1,3,4,6-tetrakis(hydroxymethyl)tetrahydroimidazo[4,5-d]imidazole-2,5(1H,3H)-dione (1.88 g, 7.2 mmol) in 1.5 ml of DMSO was dissolved. Then, 0.15 ml nitric acid (65%) and n-BuOH (13.12 ml, 143 mmol) were added to the solution and the mixture was heated at 60° C. for 16 hours. After the reaction was over, the reaction liquid was cooled and 1N NaOH was added around pH 7. Around 100 ml ethyl acetate was used to extract with mixture and the organic phase was washed by saturated NaCl(aq) solution for 2 times. After being dried by Na$_2$SO$_4$, the solvent was removed. The crude compound was purified by flash chromatography (Heptane/EtOAc). The product was obtained colorless viscous oil in 0.38 g, yield (11%) $^1$H NMR (600 MHz, DMSO-d6): δ (ppm) 5.52 (s, 2H), 4.73 (m, 8H), 3.35 (m, 8H), 1.46 (m, 8H), 1.29 (m, 8H), 0.85 (t, 12H).

Example 8: Synthesis of Tetra(Tetrahydro-4-Pyranol) Glycoluril

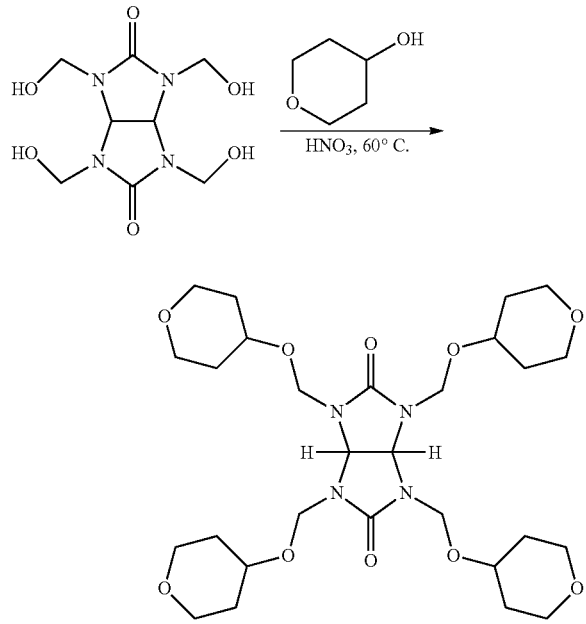

1,3,4,6-tetrakis(hydroxymethyl)tetrahydroimidazo[4,5-d]imidazole-2,5(1H,3H)-dione (3 g, 11.4 mmol) in tetrahydro-4-pyranol (11 ml, 114 mmol) was dissolved. Then, 0.15 ml nitric acid (65%) was added to the solution and the mixture was heated at 60° C. for 16 hours. After the reaction was over, the reaction liquid was cooled and 1N NaOH was added around pH 7. Around 100 ml ethyl acetate was used to extract with mixture and the organic phase was washed by saturated NaCl(aq) solution for 2 times. After being dried by $Na_2SO_4$, the solvent was removed. The crude compound was purified by flash chromatography (MC/acetone). The product was obtained colorless viscous oil. $^1$H NMR (600 MHz, DMSO-d6): δ (ppm) 5.57 (s, 2H), 4.84 (m, 8H), 3.78 (m, 8H), 3.57 (m, 4H), 3.29 (m, 8H), 1.82 (m, 8H), 1.40 (m, 8H).

Example 9: Synthesis of Tetra(4-Ethylcyclohexanol) Glycoluril

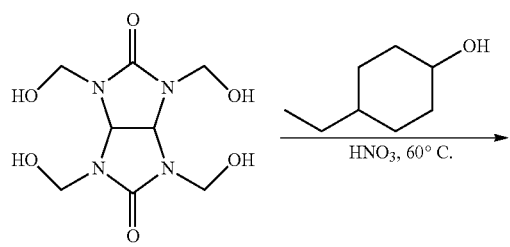

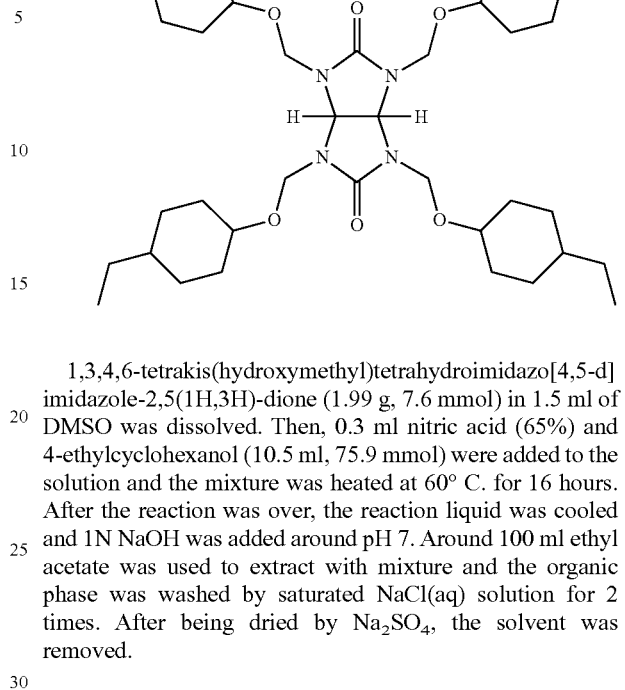

1,3,4,6-tetrakis(hydroxymethyl)tetrahydroimidazo[4,5-d]imidazole-2,5(1H,3H)-dione (1.99 g, 7.6 mmol) in 1.5 ml of DMSO was dissolved. Then, 0.3 ml nitric acid (65%) and 4-ethylcyclohexanol (10.5 ml, 75.9 mmol) were added to the solution and the mixture was heated at 60° C. for 16 hours. After the reaction was over, the reaction liquid was cooled and 1N NaOH was added around pH 7. Around 100 ml ethyl acetate was used to extract with mixture and the organic phase was washed by saturated NaCl(aq) solution for 2 times. After being dried by $Na_2SO_4$, the solvent was removed.

Example 10: Synthesis of Tetra(4-Methylcyclohexanol) Glycoluril

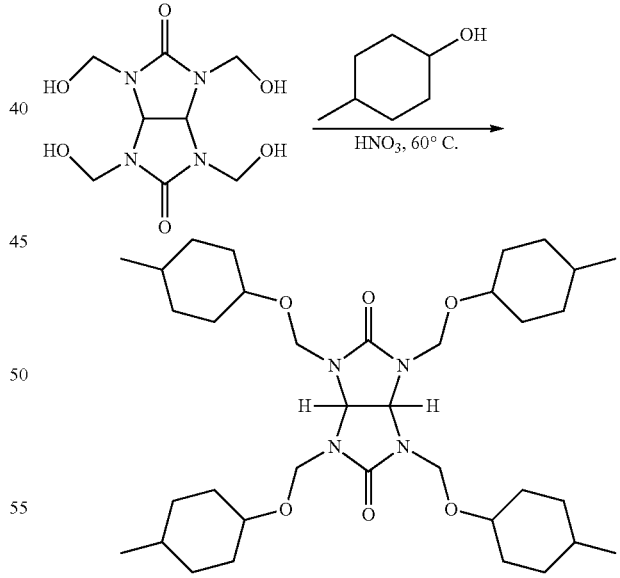

1,3,4,6-tetrakis(hydroxymethyl)tetrahydroimidazo[4,5-d]imidazole-2,5(1H,3H)-dione (1.25 g, 4.8 mmol) in 3 ml of DMSO was dissolved. Then, 0.3 ml nitric acid (65%) and 4-methylcyclohexanol (5.9 ml, 47.7 mmol) were added to the solution and the mixture was heated at 60 C for 16 hours. After the reaction was over, the reaction liquid was cooled and 1N NaOH was added around pH 7. Around 100 ml ethyl acetate was used to extract with mixture and the organic phase was washed by saturated NaCl(aq) solution for 2 times. After being dried by Na$_2$SO$_4$, the solvent was removed.

Example 11: Thermal Degradation of Cross-Linker by TGA

This example shows increased thermal degradation behavior of present cross-linker molecules as corresponds to their thermal gravimetric analysis (TGA) decomposition profiles.

As referred to herein, thermal gravimetric analysis (TGA) decomposition temperature of a sample material (particularly crosslinker compound) is determined by the following protocol. Thermal gravimetric analysis (TGA) decomposition temperature is determined by measuring mass change of the tested sample with mass spectrometry as temperature is constantly raised. As temperature increases, the weight change of the sample is measured. The temperature at which a 50 percent mass loss is recorded is determined to be the decomposition temperature of the material. A commercially available (such as PerkinElmer) thermal gravimetric analysis apparatus can be employed for the determination.

TGA decomposition temperatures for the following cross-linkers shown in Table 1 were measured. As shown in Table 1, tetrakis(cyclohexoxymethyl)glycoluril (TcyGU) has the highest decomposition temperature and is followed by the tetrakis(n-hexoxymethyl)—(TnhyGU), tetrakis(n-butoxymethyl)-(TnbGU), tetrakis(phenoxymethyl)—(TPhmGU), tetrakis(isopropoxymethyl)—(TisoproGU), and tetrakis (methoxymethyl)—(TMGU) derivatives, respectively. The structures of these crosslinker compounds area as follows:

Example 12: Strip/Swell Results with Slow Thermal Acid Generator Formulation This example shows the effectiveness of the heavy cross-linker (TcyGU) at forming a BARC during thermal baking. The control compound, tetrakis (methoxymethyl)glycoluril (TMGU), is known to vaporize during high thermal baking temperature (e.g. 205° C.) and therefore gives high strip/swell values that indicate a poor film was produced that had high solubility in the subsequent processing step under aqueous conditions. The present heavy cross-linker, TcyGU, does not vaporize at these temperatures and is very active as a cross-linker, therefore the resulting BARC film does not dissolve under the subsequent aqueous processing steps and gives low strip/swell values. As a comparison, the cross-linkers MiPGU and MP-TMGU were evaluated and did not act as an effective cross-linker at these process conditions and provided very poor strip/swell values.

Preparation of Antireflective Compositions 0.23 g TMGU (Example F1 in Table 2 below) or TcyGU (Example F2 in Table 2 below) or MiPGU (Example F3 in Table 2 below) or MP-TMGU (Example F4 in Table 2 below), 0.006 g p-TSA benzylammonium salt, 0.001 g fluorochemical surfactant Polyfox 656 from OMNOVA solutions Inc. 0.53 g isocyanurate based polyester COP-BTTB (Chemoptics, Korea, Mw=3K, PDI=1.4), and 19.2 g methyl-2-hydroxy isobutyrate (HBM) were mixed to obtain a 3.8 wt % solution, based on total weight of the composition. The solution was filtered through a PTFE micro filter with 0.45 micron pore size to obtain BARC compositions. One comparative formulation were prepared by mixing 0.23

TABLE 1

TMGU
Chemical Formula: C$_{12}$H$_{22}$N$_4$O$_6$
Molecular Weight: 318.33

TisoproGU
Chemical Formula: C$_{20}$H$_{38}$N$_4$O$_6$
Molecular Weight: 430.55

TnbuGU
Chemical Formula: C$_{24}$H$_{46}$N$_4$O$_6$
Molecular Weight: 486.65

TPhmGU
Chemical Formula: C$_{32}$H$_{30}$N$_4$O$_6$
Molecular Weight: 566.61

TcyGU
Chemical Formula: C$_{32}$H$_{54}$N$_4$O$_6$
Molecular Weight: 590.81

TnhGU
Chemical Formula: C$_{32}$H$_{62}$N$_4$O$_6$
Molecular Weight: 598.87

| | TMGU | TisoproGU | TPhmGU | TnbuGU | TnhGU | TcyGU |
|---|---|---|---|---|---|---|
| temperature (°C) | 231.08 | 213.85 | 224.74 | 257.08 | 304.44 | 332.84 | g TMGU, 0.006 g p-TSA ammonium salt, 0.001 g fluorochemical surfactant Polyfox 656 from OMNOVA solutions Inc. 0.53 g isocyanurate based polyester resin COP-BTTB (Chemoptics, Korea, Mw=3K, PDI=1.4), and 19.2 g methyl-2-hydroxy isobutyrate (HBM) (Example C1)

Procedure for Measuring Solvent Resistance (Swell/Strip)

Each sample solution tested for solvent resistance was spin-coated onto a Si wafer and baked at 205 C for 60 sec. The thickness of film on the Si wafer was measured using ellipsometry (THK at coat column at below table). PGME/PGMEA=70:30 wt % mixture solution, commonly used in photoresist art, was then poured over the surface of the BARC film and allowed to sit for 90 seconds. The wafer was then spun dry at 4000 rpm for 60 seconds. The thickness was measured again (THK at strip column at below table) and final thickness was measured one more time after additional bake at 110 C for 60 seconds (THK at bake column at below table). The difference between final bake and spun dry is reported as a swell value and the difference from initial thickness is reported as a strip value.

TABLE 2

| Sample name | Bake temp. (° C.) | Strip solvent | Coat | Strip | Bake | Strip (Bake-Coat) | Swell (Bake-Strip) |
|---|---|---|---|---|---|---|---|
| Example F1 | 205 | PGME/PGMEA | 991.97 | 444.21 | 421.47 | −570.5 | −22.7 |
| Example F2 | 205 | PGME/PGMEA | 1027.19 | 1025.84 | 1027.92 | 0.7 | 2.1 |
| Example F3 | 205 | PGME/PGMEA | 973.89 | 36.33 | 40.89 | −933.0 | 4.6 |
| Example F4 | 205 | PGME/PGMEA | 930.78 | 686.22 | 644.31 | −286.5 | −41.9 |

Example 13: Sublimation Results of BARC Thin Films Containing Various x-Linkers

This example shows the demonstrated outgassed thickness of the three best performing compounds from Example 12 under QCM baking temperatures of 205° C. The control compound, TMGU, had high outgassed thickness which is what led to the poor performance in Example 12 above. The inventive compound, TcyGU, gave very low outgassed thickness which is what led to superior performance in Example 12. The best performing comparative compound, MP-TMGU, gave the work outgassed thickness value and contributed to the poor results in Example 12 above.

Preparation of Antireflective Compositions for Sublimation Test 0.23 g TMGU (Example F5 in Table 3 below) or TcyGU (Example F6 in Table 3 below) or MP-TMGU (Example F7 in Table 3 below), 0.001 g fluorochemical surfactant Polyfox 656 from OMNOVA solutions Inc. 0.53 g isocyanurate based polyester COP-BTTB (Chemoptics, Korea, Mw=3K, PDI=1.4), and 19.2 g methyl-2-hydroxy isobutyrate (HBM) were mixed to obtain a 3.8 wt % solution, based on total weight of the composition. The solution was filtered through a PTFE micro filter with 0.45 micron pore size to obtain BARC compositions without thermal acid generator to avoid cross-linking effect on sublimation results.

General Procedure for Measuring Sublimation

Quartz crystal microbalance (QCM) was used to determine sublimation content. Each sample solution tested for sublimation was spin-coated onto a Si wafer and baked at 205 C on special hot plate that brought the wafer in nearly direct contact with a quartz crystal sample holder. The b/a frequency was measured by a frequency counter and converted into a thickness determination for the material sublimated in the QCM plate.

TABLE 3

| Sample name | QCM Bake temp. (° C.) | Outgassed Thick(Å) | Outgassed Thick(Å) Average |
|---|---|---|---|
| Example F5 | 205 | 20.5<br>20.6 | 20.6 |
| Example F6 | 205 | 6<br>8 | 7.0 |
| Example F7 | 205 | 26.8<br>26 | 26.4 |

Example 14: Lithography

This example shows that the inventive heavy cross-linker, TcyGU, produced comparable results to the reference compound, TMGU, when a photoresist was placed on top of the resulting BARC materials that contained the cross-linkers and were processed at low temperatures. This confirms the utility of the heavy cross-linker for these and other applications.

BARC compositions of Example F1 and C1 were each spin-coated on 150-mm silicon wafers at 1500 rpm, and then baked at 205° C. for 60 seconds using a TEL Mark 8 wafer coating track machine. The BARC coating thickness after bake was 1000 Å. Dow UV™1610 DUV photoresist was spin-coated on top of BARC coating and baked at 100° C. for 60 seconds to give a 240 nm thick layer of photoresist. The photoresist was next exposed through a target mask using a 248 nm KrF wafer stepper with 0.65 NA. The photoresist layer was next post-exposure baked at 120° C. for 60 seconds, and then developed using Dow MF™ CD-26 TMAH developer in a standard 60 second single puddle process. Inspection of critical dimensions of patterns by scanning electron microscopy was conducted to examine the pattern collapse margin of photoresist on each BARC.

What is claimed is:

1. A method for forming a photoresist relief image, comprising:
    a) applying on a substrate a layer of a coating composition comprising:
        1) a resin; and
        2) a crosslinker that comprises a structure of Formula (I):

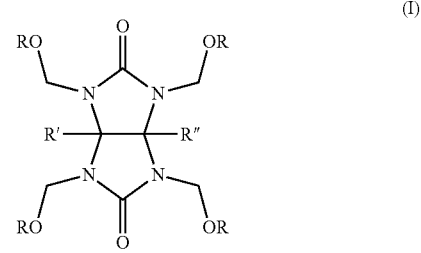

wherein in Formula (I):
each R is independently selected from hydrogen, optionally substituted alkyl, optionally substituted heteroalkyl, optionally substituted carbocyclic aryl, or optionally substituted heteroaryl,
with at least one R group being a cyclohexyl moiety;
R' and R" are each independently selected from hydrogen, optionally substituted alkyl or optionally substituted heteroalkyl, optionally substituted carbocyclic aryl, or optionally substituted heteroaryl; and b) applying a layer of a photoresist composition above the coating composition layer; and c) imaging the photoresist composition layer and developing the imaged photoresist composition layer.

2. The method of claim 1 wherein the crosslinker component has a molecular weight of at least 400 daltons.

3. The method of claim 1 wherein the crosslinker component has a molecular weight of less than 1500 daltons.

4. The method of claim 1 wherein the crosslinker component has a degradation temperature of greater than 250° C.

5. The method of claim 1 wherein each R group is other than hydrogen.

6. The method of claim 1 wherein the coating composition layer is thermally treated to cure the composition coating layer before applying the photoresist composition layer.

7. The method of claim 1 wherein the crosslinker is selected from the group consisting of the following structures:

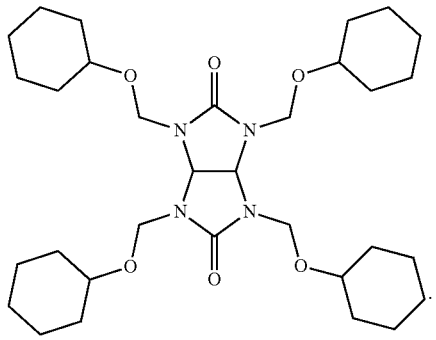 [SMILES: O=C1N(COC2CCCCC2)C2C(N1COC1CCCCC1)N(COC1CCCCC1)C(=O)N2COC1CCCCC1]

8. A coated substrate comprising:
a substrate having thereon:
a) a coating composition comprising:
  1) a resin; and
  2) a crosslinker component;
b) a layer of a photoresist composition above the coating composition layer,
wherein the crosslinker component prior to reaction with the resin comprises a structure of Formula (I):

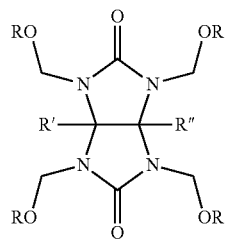

(I)

wherein in Formula (I):
each R is independently selected from hydrogen, optionally substituted alkyl, optionally substituted heteroalkyl, optionally substituted carbocyclic aryl, or optionally substituted heteroaryl,
with at least one R being a cyclohexyl moiety;
R' and R" are each independently selected from hydrogen, optionally substituted alkyl or optionally substituted heteroalkyl, optionally substituted carbocyclic aryl, or optionally substituted heteroaryl.

9. The coated substrate of claim 8 wherein the crosslinker is:

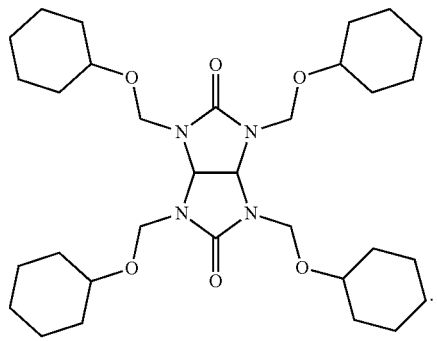 [SMILES: O=C1N(COC2CCCCC2)C2C(N1COC1CCCCC1)N(COC1CCCCC1)C(=O)N2COC1CCCCC1]

10. A crosslinker that comprises a structure selected from:

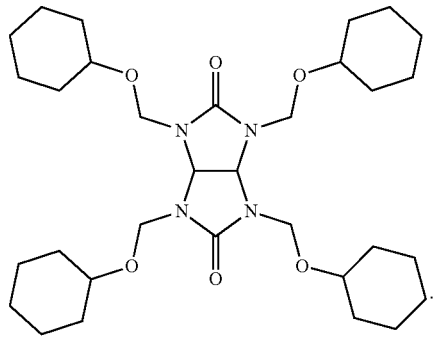 [SMILES: O=C1N(COC2CCCCC2)C2C(N1COC1CCCCC1)N(COC1CCCCC1)C(=O)N2COC1CCCCC1]

11. The crosslinker of claim 10 wherein the crosslinker comprises the following structure:

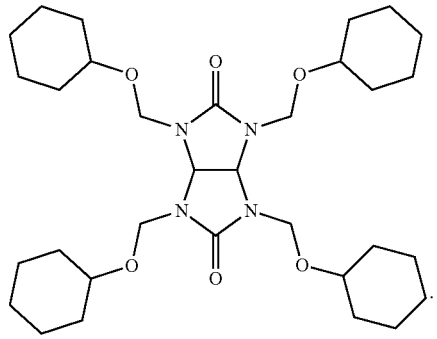 [SMILES: O=C1N(COC2CCCCC2)C2C(N1COC1CCCCC1)N(COC1CCCCC1)C(=O)N2COC1CCCCC1]

12. A coating composition for use with an overcoated photoresist, the coating comprising:
1) a resin; and
2) a crosslinker that comprises a structure of Formula (I):

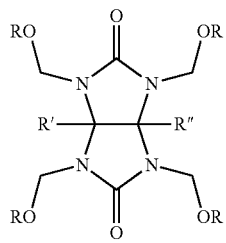

(I)

wherein in Formula (I):

each R is independently selected from hydrogen, optionally substituted alkyl, optionally substituted heteroalkyl, optionally substituted carbocyclic aryl, or optionally substituted heteroaryl, with at least one R group comprises an optionally substituted cyclohexyl group;

R' and R" are each independently selected from hydrogen, optionally substituted alkyl or optionally substituted heteroalkyl, optionally substituted carbocyclic aryl, or optionally substituted heteroaryl.

13. The composition of claim 12 wherein the crosslinker comprises the following structure:

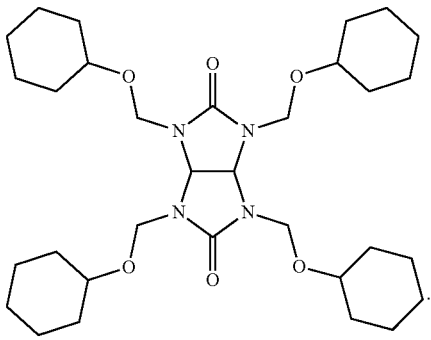 [SMILES: O=C1N(COC2CCCCC2)C2C(N1COC1CCCCC1)N(COC1CCCCC1)C(=O)N2COC1CCCCC1]

* * * * *